(12) United States Patent
Yang

(10) Patent No.: US 6,984,212 B1
(45) Date of Patent: Jan. 10, 2006

(54) ELECTRONIC SPHYGMOMANOMETER CALIBRATING TOOL

(75) Inventor: Paul Yang, Chung Ho (TW)

(73) Assignee: Health & Life Co., Ltd., Taipei (TW)

( * ) Notice: Subject to any disclaimer, the term of this patent is extended or adjusted under 35 U.S.C. 154(b) by 0 days.

(21) Appl. No.: 10/944,766

(22) Filed: Sep. 21, 2004

(51) Int. Cl.
*A61B 5/02* (2006.01)
(52) U.S. Cl. ..................................... 600/490
(58) Field of Classification Search ............... 600/490, 600/492–499; 434/266–268, 262, 272
See application file for complete search history.

(56) References Cited

U.S. PATENT DOCUMENTS

| | | | | |
|---|---|---|---|---|
| 4,464,123 A | * | 8/1984 | Glover et al. | 434/268 |
| 4,471,646 A | * | 9/1984 | Walker | 73/1.67 |
| 5,016,466 A | * | 5/1991 | Ness et al. | 73/1.64 |
| 6,699,196 B2 | * | 3/2004 | Hung | 600/494 |

* cited by examiner

Primary Examiner—Robert L. Nasser
Assistant Examiner—Navin Natnithithadha

(74) Attorney, Agent, or Firm—Bacon & Thomas PLLC

(57) ABSTRACT

The present invention discloses an electronic sphygmomanometer calibrating tool, which comprises a platform being coupled to a control system; at least one tool being disposed on the platform for accommodating a testing electronic sphygmomanometer, and the tools being individually coupled to the platform and a pressurizing device through an electric circuit and a gas pipeline; a pulse signal blood pressure simulator being coupled to the gas pipeline, such that when the electronic sphygmomanometer is calibrated, the pressurizing device pressurizes the testing electronic sphygmomanometer by pressurizing the gas pipeline and the control system set the initial state and the maximum pressure for the testing electronic sphygmomanometer. Since the values of the blood pressure from the initial state to the maximum value in increased linearly, therefore the control system can calculate the rest of the values to calibrate the testing electronic sphygmomanometer. Then, the pulse signal blood pressure simulator is turned on to set the pulse blood pressure for the testing electronic sphygmomanometer. Therefore, more than one electronic sphygmomanometer can be set up and calibrated at the same time by the interconnecting structure between the control system and the tools in order to save time and improve the precision of the calibration.

4 Claims, 3 Drawing Sheets

ELECTRONIC SPHYGMOMANOMETER CALIBRATING TOOL

BACKGROUND OF THE INVENTION

1. Field of the Invention

The present invention relates to an electronic sphygmomanometer calibrating tool, more particularly to a calibrating tool that makes use of the interconnection between tools to allow manufacturers to calibrate two or more testing electronic sphygmomanometers at the same time as to save time and enhance precision.

2. Description of the Related Art

In general, a traditional electronic sphygmomanometer has to go through the setup and calibration procedures before it is shipped out of the factory. The calibration and setup are performed manually; in which a circuit board of the electronic sphygmomanometer, a control system and an air pump are connected, and then the circuit board of the electronic sphygmomanometer is manually set to an initial state, such that air is pumped into the pressure sensor of the circuit board on the testing electronic sphygmomanometer by the air pump until the air pressure reaches the maximum set value. A variable resistor (VR) is changed manually to set the maximum set value for the circuit board. However, such method can only calibrate one electronic sphygmomanometer at a time, and also requires a manual operation for the calibration. Such method not only is inefficient, but also wastes a great deal of manpower, cost and time.

SUMMARY OF THE INVENTION

In view of the foregoing shortcomings of the prior art, the inventor of the present invention focused on the problem to start finding a way for the improvement and overcome the shortcomings in hope of finding a feasible solution, and conducted extensive researches and experiments and finally invented the electronic sphygmomanometer calibrating tool in accordance with the present invention.

Therefore, it is the primary objective of the present invention to provide an electronic sphygmomanometer, which comprises a platform; at least one press button being disposed on the platform and connected to a control system for controlling the operation of the electronic sphygmomanometer; at least one tool being disposed on the platform for accommodating the testing electronic sphygmomanometer, and these tools individually having an interconnected gas pipeline, and these interconnected gas pipelines being coupled to a pressurizing device. An electric contact point and an air hole are disposed on each of the tools corresponding to the testing electronic sphygmomanometer; wherein the air hole is interconnected with the gas pipelines, such that the air in the gas pipeline will be discharged until its pressure is equal to the atmospheric pressure (which is the initial state) according to the instruction given by pressing the press button during the test. The control system will set the testing electronic sphygmomanometer to a maximum pressure, and then compute the value corresponding to each pressure value by the linear slope relation from the maximum pressure value to the initial state. The values obtained are used for calibrating the testing electronic sphygmomanometer. Therefore, more than one electronic sphygmomanometer can be set and calibrated at the same time by the interconnecting structure between the control system and the tools in order to save time and improve the precision of the calibration.

Another objective of the present invention is to provide an electronic sphygmomanometer calibrating tool, wherein the gas pipeline is connected to a pulse signal blood pressure simulator, and a press button is disposed on a platform for controlling the pulse signal blood pressure simulator, so that if the press button is pressed to turn on the pulse signal blood pressure simulator, the pulse signal blood pressure simulator will send a specific simulated pulse pressure to each of the testing electronic sphygmomanometer on each tool through the gas pipeline and drive the control system to assign the specific simulated pressure to the testing electronic sphygmomanometers as to complete the pulse pressure setup for the testing electronic sphygmomanometers.

A further objective of the present invention is to provide an electronic sphygmomanometer calibrating tool, wherein the pressurizing device comprises a gas storage tank, being connected to an air pump, so that when the electronic sphygmomanometer is in use, air is pumped and stored into the gas storage tank by the air pump and the air can be sent evenly and steadily to each of the tools through the gas pipeline.

BRIEF DESCRIPTION OF THE DRAWINGS

The above objects, features and advantages of the present invention will become apparent from the following detailed description taken with the accompanying drawing.

DETAILED DESCRIPTION OF THE PREFERRED EMBODIMENTS

Figure 1:
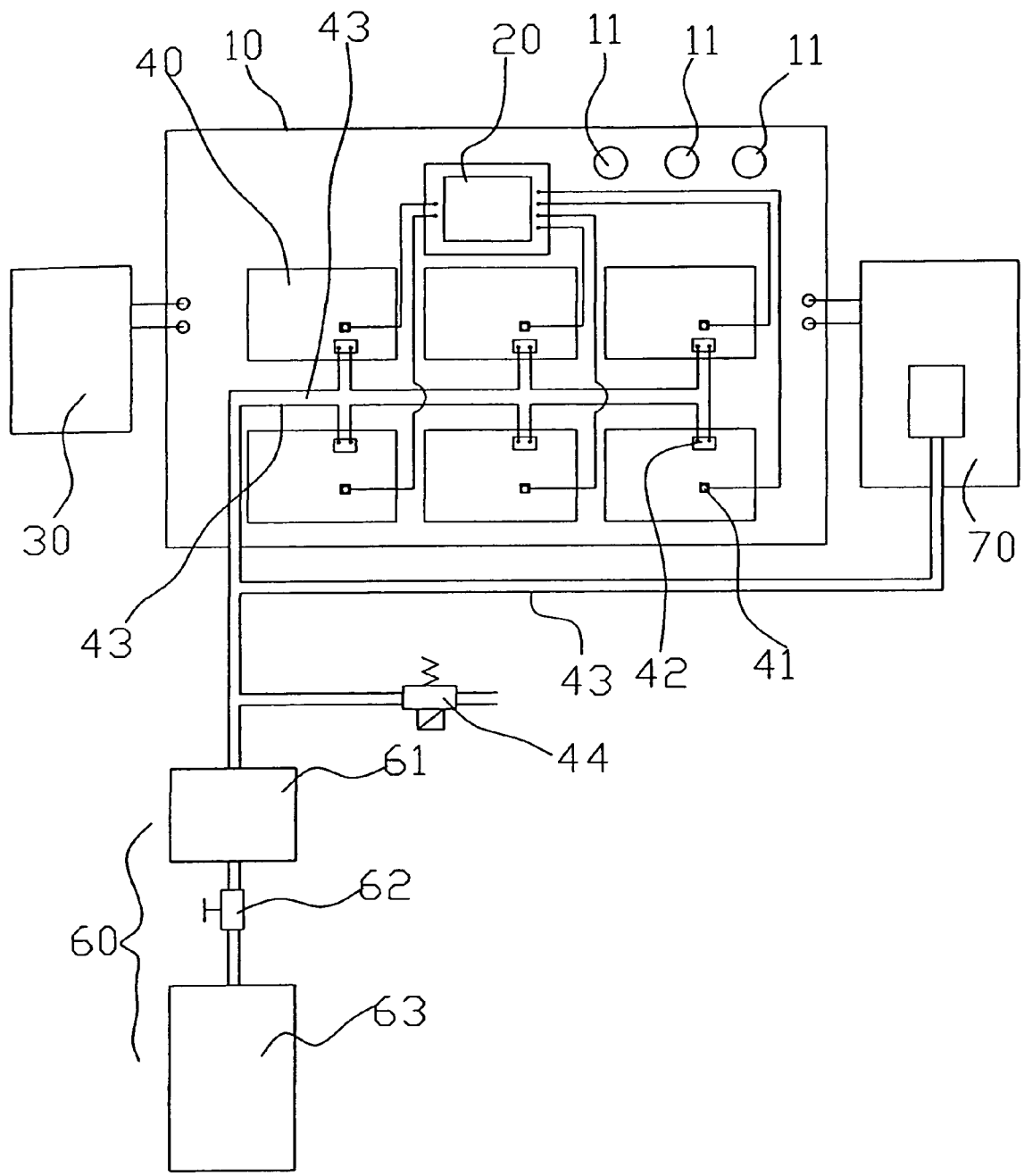
FIG. 1 is an illustrative view of the electronic sphygmomanometer calibrating tool according to the present invention when the testing electronic sphygmomanometer is not placed on the platform.

Please refer to FIG. 1 for an electronic sphygmomanometer calibrating tool according to the present invention. The electronic sphygmomanometer calibrating tool is used to calibrate an electronic sphygmomanometer before the electronic sphygmomanometer exits the factory. The electronic sphygmomanometer calibrating tool comprises: a platform 10; at least one press button 11 being disposed on the platform 10, and three press buttons 11 are used in this embodiment, wherein one is for controlling the air pressure of the initial state, the other one for controlling the air pressure to reach the maximum value, and the last one for enabling the pulse; a display device 20 being disposed on the platform 10, and a control system 30 being electrically coupled with the platform 10 by an electric circuit.

Further, the platform 10 comprises at least one tool 40 thereon, and the tools 40 are built according to the testing electronic sphygmomanometer, and the tools 40 are connected to the display device 20 and the control system 30 through the electric circuit. The tool 40 also comprises an electric contact point 41 and an air hole 42 corresponding to each testing electronic sphygmomanometer; wherein the air holes 42 are connected to the gas pipelines 43, and the gas pipelines 43 are interconnected, and the gas pipeline 43 are extended outward to couple with a pressurizing device 60. A gas storage tank 61 is disposed on the pressurizing device 60 and coupled to an adjusting valve 62 and an air pump 63 for supplying air. Further, the gas pipeline 43 has an air valve 44 on a specific position of the gas pipeline 43.

The gas pipeline 43 is connected to a pulse signal blood pressure simulator 70, and the pulse signal blood pressure simulator 70 is used to simulate the pulse signal, and the pulse signal blood pressure simulator 70 is connected to a press button 11 of the platform 10 by the electric circuit.

Figure 2:
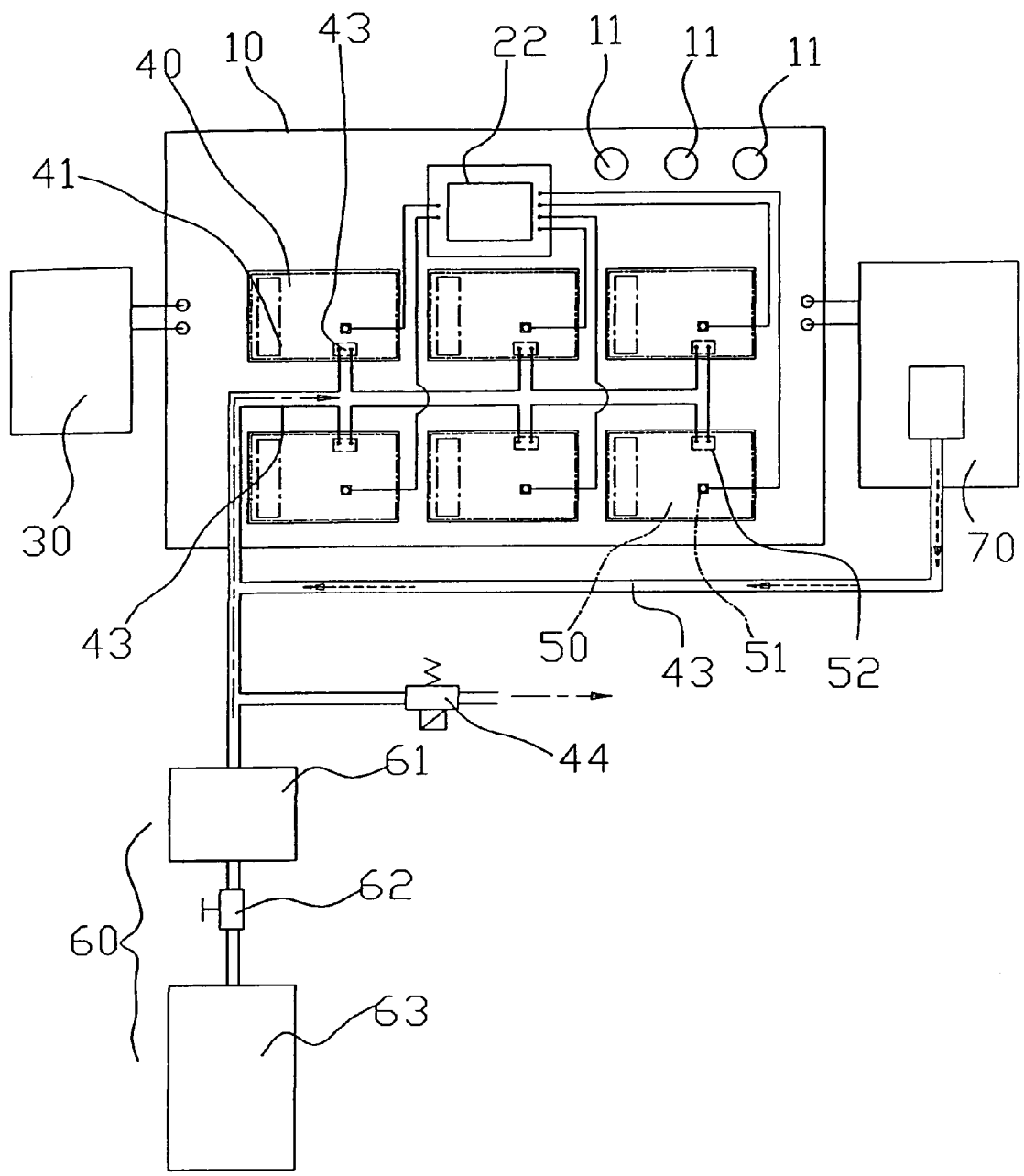
FIG. 2 is an illustrative view of the electronic sphygmomanometer calibrating tool according to the present invention when the testing electronic sphygmomanometer is placed on the platform.
Figure 3:
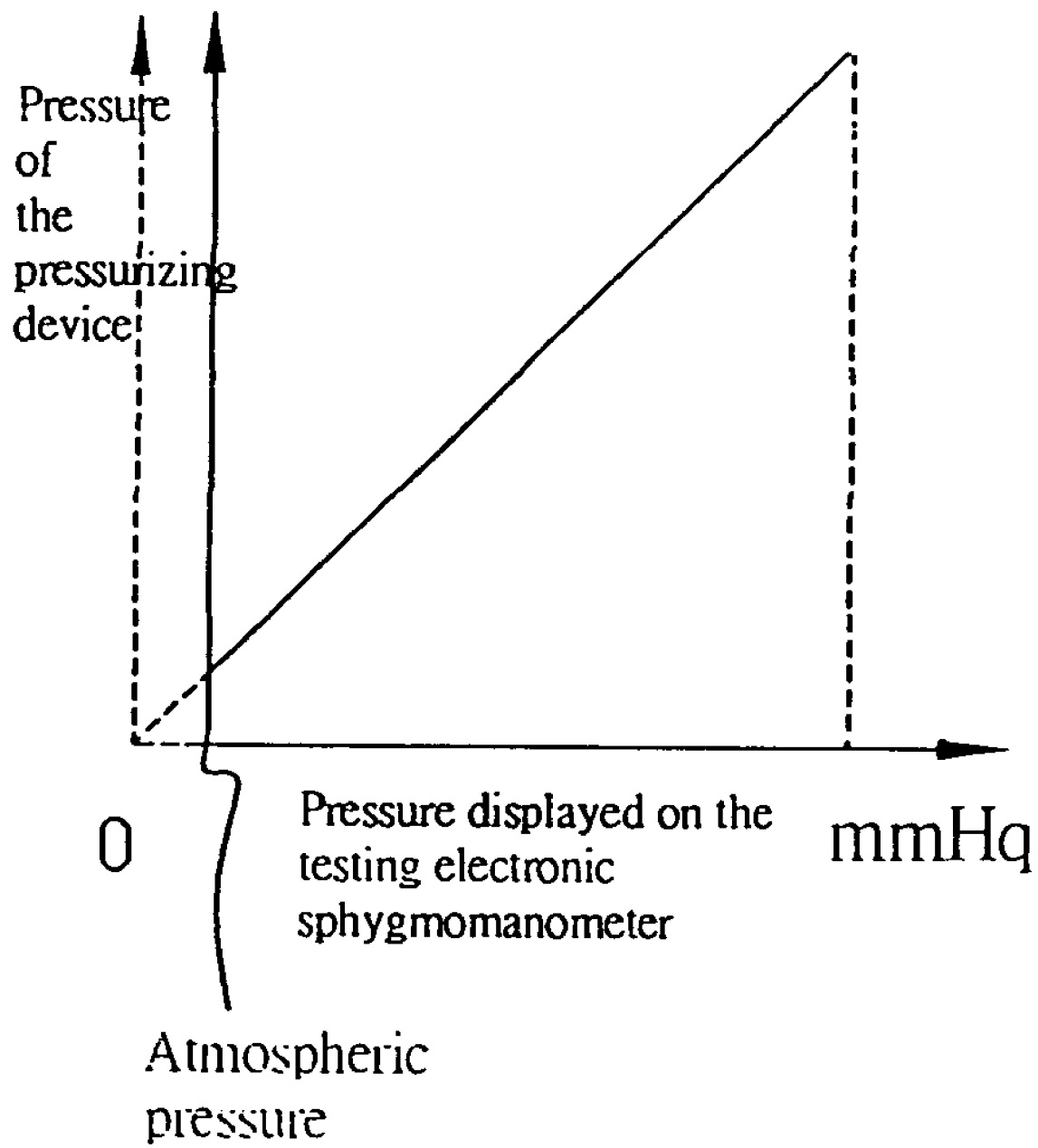
FIG. 3 is a curve of the pressure of the pressurizing device versus the pressure of the testing electronic sphygmomanometer from the initial state to the maximum pressure according to the present invention.

Please refer to FIG. 2. Since the electronic sphygmomanometer 50 is calibrated according to the present invention before shipping out of the factory, and the main components of a general electronic sphygmomanometer 50 and the display device 20 are placed on a circuit board 50, and thus the present invention will focus on the circuit board 50 for the calibration. Therefore, when the calibration is performed, the foregoing circuit boards 50 are put into the tools 40 individually, such that the electric contact point 51 and the air hole 52 of the circuit boards 50 correspond to the electric contact point 41 and the air hole 42 of the tools 40 respectively, such that the circuit boards 50 can be connected to the control system 30 and the gas pipeline 43, and operators can press the press button 11 on the platform 10 to discharge the air in the gas pipeline through the air valve 44, and thus the pressure inside the gas pipeline is maintained at the atmospheric pressure. The control system 30 will set the air pressure state to the initial state and send the setting to the circuit board 50 of each tool 40, and then another press button 11 is pressed, such that the air in the gas storage tank 61 is distributed and sent to the circuit board 50 through the gas pipeline 43 until the display device 20 displays the maximum set value. Similarly, the control system 30 sets that state to the maximum pressure state and sends the set value of such state to the circuit board 50 of each tool 40. By the linear proportion relation from the maximum pressure value to the initial state (as shown in FIG. 3), the control system 30 will calculate the value for each corresponding pressure value according to the linear proportion relation, and the calculated results are used for setting and calibrating the testing electronic sphygmomanometer. The press button 11 of the pulse signal blood pressure simulator 70 is pressed and started to send a specific simulated pulse pressure value to the circuit board 50 of the tool 40 through the gas pipeline 43. The control system calculates and sets the blood pressure relation according to the specified pulse pressure value. Therefore, with the control of the control system 30 and the interconnection of the tools 40, more than one electronic sphygmomanometer can be set and calibrated at the same time as to save time and enhance the precision of the calibration.

In summation of the above description, the electronic sphygmomanometer calibrating tool according to present invention herein enhances the performance than the conventional structure and further complies with the patent application requirements and is submitted to the Patent and Trademark Office for review and granting of the commensurate patent rights.

While the invention has been described by way of examples and in terms of preferred embodiments, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures.

What is claimed is:

1. An electronic sphygmomanometer calibrating tool, comprising:
   a platform;
   a control system, being coupled with said platform;
   a display device, being disposed on said platform;
   at least one tool, being disposed on said platform for separately accommodating a testing electronic sphygmomanometer, and said tools being interconnected by a gas pipeline and having an electric contact point thereon and said electric contact point being coupled with said platform and said testing electronic sphygmomanometer;
   a pressurizing device, being coupled with a gas pipeline for pressurizing said testing electronic sphygmomanometer on said tools and
   a pulse signal blood pressure simulator, being coupled to said tool sand said platform through said air pipeline and an electric circuit;
   wherein, when said electronic sphygmomanometer is calibrated, said pressurizing device pressurizes said testing electronic sphygmomanometer on said tool through said gas pipeline, and after a control system sets an initial state and a maximum pressure for said testing electronic sphygmomanometer, said control system is capable of calculating the pressure values for said testing electronic sphygmomanometer according to the linear increasing slope relation between said initial state and said maximum pressure as to calibrate said testing electronic sphygmomanometer; and wherein said pulse signal blood pressure simulator is turned on to set a pulse signal blood pressure for said testing electronic sphygmomanometer, such that said control system is capable of controlling the setup and calibration for more than one electronic sphygmomanometer at the same time.

2. The electronic sphygmomanometer calibrating tool of claim 1, wherein said platform comprises at least one press button.

3. The electronic sphygmomanometer calibrating tool of claim 1, wherein said pressurizing device comprises a gas storage tank being coupled to an air pump, such that when the electronic sphygmomanometer is in use, said air pump pumps air into said gas storage tank, and air is sent evenly and steadily to said each tool through said gas pipeline.

4. The electronic sphygmomanometer calibrating tool of claim 1, wherein said display device is a liquid crystal display device.

* * * * *